United States Patent [19]

Seper et al.

[11] Patent Number: 5,935,560
[45] Date of Patent: *Aug. 10, 1999

[54] COMPOSITION AND METHODS OF IMPARTING DURABLE CONDITIONING PROPERTIES TO HAIR

[75] Inventors: Jennifer M. Seper, Westmont; Paul H. Neill, Hinsdale; Arun Nandagiri, Libertyville, all of Ill.

[73] Assignee: Helene Curtis, Inc., Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/712,560

[22] Filed: Sep. 13, 1996

[51] Int. Cl.⁶ .................. A61K 7/11; A61K 7/06
[52] U.S. Cl. .................. 424/70.12; 424/70.122; 424/70.5; 424/70.2; 424/70.6
[58] Field of Search .................. 424/70.12, 70.122, 424/70.5, 70.2, 70.6; 132/203

[56] References Cited

U.S. PATENT DOCUMENTS

| | | |
|---|---|---|
| 4,970,067 | 11/1990 | Panandiker et al. .................. 424/70 |
| 4,973,475 | 11/1990 | Schnetzinger et al. .................. 424/70.122 |
| 5,085,858 | 2/1992 | Halloran et al. .................. 424/70.5 |
| 5,270,036 | 12/1993 | Varaprath et al. .................. 424/71 |
| 5,279,818 | 1/1994 | Halloran et al. .................. 424/71 |
| 5,362,485 | 11/1994 | Hayama et al. .................. 424/70.5 |
| 5,637,295 | 6/1997 | Lang et al. .................. 424/70.5 |

FOREIGN PATENT DOCUMENTS

| | | |
|---|---|---|
| 845 277 | 6/1970 | Canada . |
| 0 295 780 | 12/1988 | European Pat. Off. . |
| 1 182 939 | 6/1967 | United Kingdom . |

*Primary Examiner*—Sally Gardner-Lane
*Attorney, Agent, or Firm*—Milton L. Honig

[57] ABSTRACT

A composition and method of conditioning hair and imparting durable conditioning properties to the hair are disclosed. The composition contains a thiol-functional silicone, and is applied to natural unreduced hair. After applying the composition to hair, the hair can be rinsed with water or treated with a neutralizing solution. The method and composition impart unexpectedly durable hair-conditioning properties to treated hair.

15 Claims, 8 Drawing Sheets

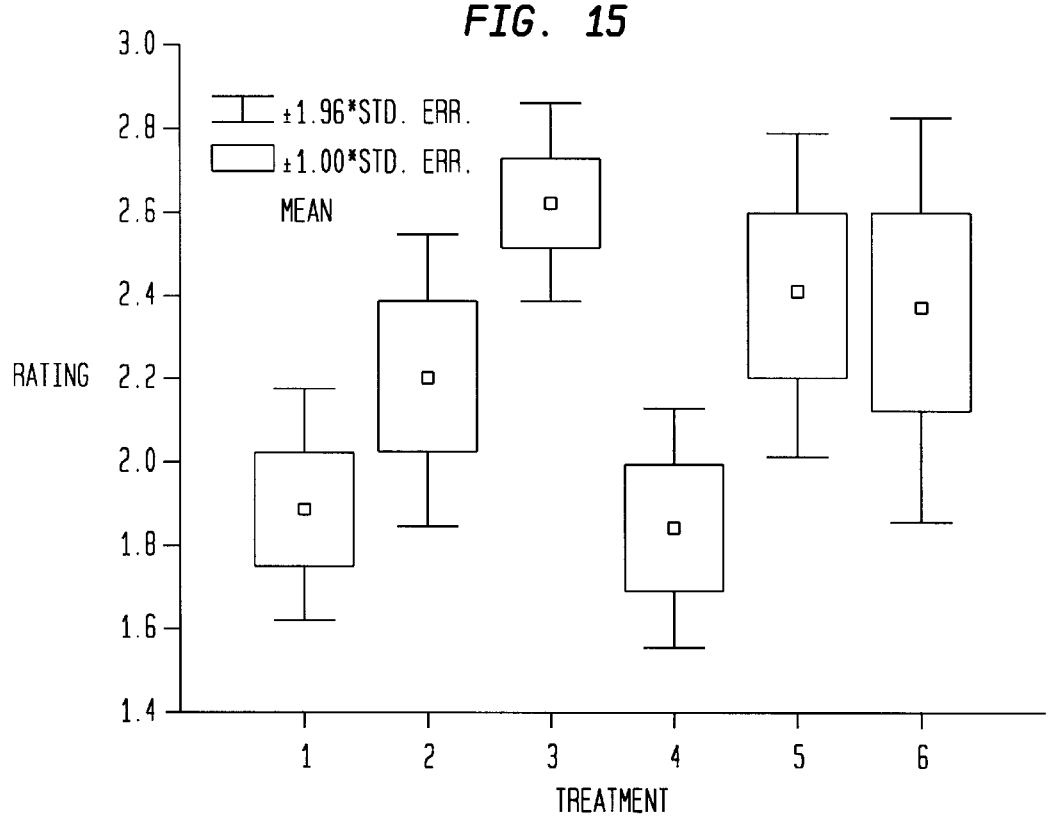

COMPOSITION AND METHODS OF IMPARTING DURABLE CONDITIONING PROPERTIES TO HAIR

FIELD OF THE INVENTION

The present invention relates to compositions and to methods of treating keratin fibers, including human hair and wool, that condition the fibers and impart unexpectedly durable conditioning properties to the fibers. More particularly, the present invention is directed to a hair-treating composition comprising about 0.1% to about 5% of a thiol-functional silicone, which imparts unexpectedly durable hair conditioning properties to treated hair. The composition of the present invention can be applied to unreduced hair or to reduced hair. After applying the composition to the hair, the hair then is rinsed or can be treated with a neutralizing solution. The hair-treating composition of the present invention can be applied to the hair from an aqueous solution or spray, a hydroalcoholic solution or spray, an emulsion, a conditioner, a shampoo, or other similar hair-treating product.

BACKGROUND OF THE INVENTION

Most individuals buy and use a hair shampoo for its cleansing properties. In addition to clean hair, consumers also desire sufficiently conditioned hair that holds a preset configuration. However, present-day hair shampoos generally are formulated with highly effective synthetic surfactants, like anionic surfactants, that primarily clean, as opposed to condition, the hair. Therefore, it is not surprising that hair shampoos usually neither help detangle wet hair nor impart any residual hair conditioning benefits to dry hair, such as the manageability or styleability of hair sets.

Consequently, after shampooing, hair typically is left in a cosmetically unsatisfactory state because an anionic surfactant-based hair shampoo not only removes all of the dirt and soil from the hair, but also removes essentially all of the sebum that is naturally present on the surface of hair fibers. Therefore, the properties of anionic surfactants that effectively cleanse the hair also serve to leave the hair in a cosmetically unsatisfactory condition. In general, therefore, shampooing hair with a hair shampoo composition including anionic surfactants, or nonionic surfactants or amphoteric surfactants, leaves the hair, after rinsing with water, with an undesirable harsh, dull, and dry touch or feel, usually called "creak."

As a result, thoroughly cleansed hair, in either the wet or dry stage, is extremely difficult to comb because individual hair fibers tend to snarl, kink, and interlock with each other. In addition, incompletely dried hair, such as hair dried with a towel, has poor brushing properties. Then, after complete drying, the hair does not set well, and the combing or brushing property of the dried hair remains poor. The dried hair also has undesirable electrostatic properties in a low humidity atmosphere that cause the hair to "fly away," thereby further reducing the brushing property of the hair. The unsatisfactory combing or brushing property of freshly shampooed hair also causes hair damage, such as split ends or hair breakage. In addition, the natural luster and resiliency of the hair is reduced. One approach to overcoming this deficiency in normal shampoos is the use of silicones in the shampoo base. This approach still does not provide durable conditioning benefits.

Accordingly, freshly shampooed hair usually requires a post-shampoo hair treatment with a conditioning composition to improve the unsatisfactory physical and cosmetic condition of the hair. A conditioning composition traditionally is applied separately from the hair shampoo, and usually is a rinse or a cream-like lotion containing a cationic and/or a silicone compound.

However, a major disadvantage of conventional conditioners is a lack of durability of the conditioning properties imparted to the hair. Typically, shampooing the hair substantially eliminates the conditioner from the hair, thereby necessitating a reapplication of the conditioning compound to the hair after each shampoo. Shampooing removes some traditional conditioners from the hair because many conditioners, such as silicones, are not substantive to the hair and are substantially removed by anionic and nonionic surfactants in the shampoo. Other conditioners, such as the cationic quaternary ammonium compounds, are substantive to the hair, but are not covalently bound to the hair. The cationic conditioning compounds are electrostatically bound to sites on the hair having a negative electronic charge. These conditioners also are substantially removed from the hair by anionic surfactants, which have a negative electronic charge and can electrostatically bind to cationic conditioning compounds.

Accordingly, to overcome this disadvantage, investigators have sought compounds capable of covalently bonding to the hair, and methods of covalently bonding the compounds to the hair, to impart durable hair conditioning properties to hair. Investigations in this area have focused on covalently bonding a conditioning compound to the hair during a permanent waving process, especially in connection with the step of reducing the hair with a waving lotion.

In general, the permanent waving of keratin fibers, like human hair, is achieved by first chemically breaking the sulfur-to-sulfur bonds, or disulfide cystine bonds, which are naturally present in human hair, and then reforming the cystine bonds after the hair is configured in a desired hair set. The sulfur-to-sulfur cystine bonds in human hair maintain the hair in a naturally straight or naturally curly configuration, and, in order to permanently reshape the hair into a lasting, different configuration, a substantial number of the sulfur-to-sulfur bonds are broken, and then reestablished after the hair is reconfigured in a desired hair set, such as wrapped around a suitable mandrel or roller. In general, the sulfur-to-sulfur cystine bonds are broken, i.e., the hair is reduced, using a composition termed a waving lotion, which contains a reducing agent. After the reduced hair is reconfigured, the sulfur-to-sulfur cystine bonds are relinked or reestablished while the reduced hair is in the curled formation by contacting the reconfigured hair with a composition termed a neutralizing solution, which contains an oxidizing agent, such as hydrogen peroxide or a water-soluble bromate.

Waving lotions capable of breaking sulfur-to-sulfur cystine bonds in hair traditionally include one or more reducing agents, such as cysteine, acidic sodium hyposulfite, ammonium or sodium bisulfite, thioglycerol, thiolactic acid or a salt thereof, thioglycolic acid or a salt thereof, e.g., a thioglycolate, dithioglycolic acid, and/or a salt thereof, e.g., a dithioglycolate, thiocholine or a salt thereof, a monothioglycolic acid ester, N-acetylcysteamine, cysteamine, or mixtures thereof.

Generally, the waving lotion is applied to freshly shampooed hair, either before or after the hair is configured in a desired hairstyle. When the beauty operator determines that the waving lotion has been in contact with the hair for a sufficient time period to reduce the hair, the hair is rinsed thoroughly. Then a neutralizing solution is applied to the hair to oxidize the hair and reform the sulfur-to-sulfur bonds while the hair is set in the new hairstyle. The neutralizing solution contains an oxidizing agent, such as hydrogen peroxide or a bromate salt, in order to reestablish the sulfur-to-sulfur bonds and set the hair in a new and relatively permanent, e.g., about 2 to 4 months, configuration.

Investigators attempted to take advantage of reduced hair by covalently bonding compounds to the reduced hair to provide a desired effect. For example, GB 1,182,939 discloses contacting the hair with a thiol-functional silicone after the hair is reduced, and prior to oxidizing the hair, to impart a longer lasting hairstyle and retain the natural characteristics of the hair. Similarly, Canadian Patent No. 845,277 discloses application of a thiol-functional silicone to the hair after the hair is reduced.

Varaprath et al. U.S. Pat. No. 5,270,036 and Halloran et al. U.S. Pat. No. 5,279,818 disclose treating reduced hair with a neutralizing solution containing a vinyl-functional silicone. Each patent discloses covalently bonding a vinyl-functional silicone compound to the hair to achieve a benefit of conditioning or hair set retention.

EP 0 295 780 discloses simultaneously applying a reducing agent and a thiol-functional silicone to the hair. EP 0 295 780 discloses that the stepwise method disclosed in above-discussed GB 1,182,939 has disadvantages that are overcome by a method that simultaneously applies the reducing agent and thiol-functional silicone to the hair.

Other investigators applied hair treatment compounds to hair in its natural state. For example, Panandiker et al. U.S. Pat. No. 4,970,067 discloses contacting the hair with a protein having a disulfide-containing amino acid to impart durable hair set retention conditioning properties to treated hair.

Accordingly, prior methods of achieving a covalent bond between hair and a hair-treating compound relied primarily on first reducing the hair, then applying a hair-treating compound that can covalently bond to the reduced hair, and finally oxidizing the reduced hair to form a covalent bond with the hair-treating compound. The compound covalently bonded to the hair typically is hydrophobic. A hydrophobic compound reduces the tendency of hair to absorb moisture, and hence hair set retention is improved. A secondary effect of covalently bonding the compound to hair was to provide conditioning properties.

However, the need still exists for a hair-treating composition that imparts long-lasting conditioning properties to hair without the need to subject the hair to damaging hair reduction and oxidation steps. A majority of consumers consciously avoid the hair damaging effects associated with the reducing step of a permanent wave process, and, accordingly, would not accept an additional time-consuming and damaging process step to impart durable conditioning properties to hair. Furthermore, to a consumer, it is intuitively incongruent to utilize a composition and method of improving the condition of the hair which first requires damaging the hair by a hair reduction step.

Accordingly, to date, the compositions and methods used to impart durable conditioning properties to hair have suffered from poor efficacy, from sacrificing one beneficial hair property in order to achieve another beneficial hair property, and/or from abnormally long times to treat the hair. In addition, the compositions and methods previously used to semipermanently condition the hair suffer from the disadvantages of serious hair damage due to the reduction-oxidation process, coupled with operator error, such as too strong of waving lotion or too long of a contact time. Prior to the present invention, no known method or composition has been employed which effectively treats hair in a few minutes to impart durable conditioning properties that are preserved through at least several shampooings subsequent to the hair treatment.

Therefore, in accordance with the present invention, the durability of hair conditioning properties are surprisingly and unexpectedly improved by a method of contacting the hair with a composition comprising a thiol-functional silicone. The aqueous compositions of the present invention can be applied to the hair at room temperature and provide the benefits and advantages of imparting semipermanent hair conditioning properties to treated hair without the need to damage the hair as a result of harsh reduction and oxidation reactions. As demonstrated more fully hereafter, the methods of the present invention allow treatment of unreduced hair, or reduced hair that has been contacted with a waving lotion. Furthermore, for treated unreduced hair, or for treated hair reduced with a bisulfite salt, an oxidation step can be omitted and durable hair-conditioning properties are observed. Overall, the methods and compositions of the present invention impart esthetically pleasing, semipermanent hair conditioning properties to treated hair, without damaging the hair. The hair-conditioning properties are sufficiently durable to survive through many subsequent shampooings, hence the hair does not have to be conditioned after each shampooing.

SUMMARY OF THE INVENTION

The present invention relates to compositions and methods of treating keratin fibers. More particularly, the present invention relates to a method of treating the fibers, whereby contacting the fibers with a composition including a thiol-functional silicone imparts durable conditioning properties, such as gloss, combability, softness, and body, to the treated hair. Surprisingly and unexpectedly, keratin fibers, such as human hair or wool, treated with a composition of the present invention exhibit improved durability of conditioning properties, such that the fibers can be rewet or shampooed numerous times, e.g., at least six times, after application of the composition without having to reapply the composition. Furthermore, the compositions and methods of the present invention impart durable conditioning characteristics to the hair without damaging the hair, i.e., a harsh chemical reduction-oxidation process is obviated.

Therefore, one aspect of the present invention is to provide a hair-treating composition that conditions the hair and imparts semipermanent hair conditioning properties to the hair without damaging the hair.

Another aspect of the present invention is to provide a hair-treating composition comprising a sufficient amount of a thiol-functional silicone capable of covalently bonding to hair to impart conditioning properties to treated hair.

Another aspect of the present invention is to provide a hair-treating composition that is capable of imparting durable hair conditioning properties to hair over a pH range of about 3 to about 9.

Another aspect of the present invention is to provide a method of treating hair with a hair-treating composition to impart durable hair conditioning properties/styling to the hair.

Another aspect of the present invention is to provide a method of treating hair by: (a) contacting the hair with a composition having a pH of about 3 to about 9, and comprising about 0.1% to about 5% by weight of thiol-functional silicone, said thiol-functional silicone containing sufficient thiol groups to covalently bond to hair; (b) then rinsing the hair, to condition the hair and impart conditioning properties having sufficient durability to withstand many subsequent hair shampooings.

Another aspect of the present invention is to provide a hair-treating composition capable of breaking sulfur-to-sulfur bonds in the hair, wherein the composition is free of an auxiliary reducing agent, and, therefore, causes no damage to normal hair, or no further damage to tinted, frosted, bleached, or other substantially damaged hair.

Still another object of the present invention is to provide a method of treating hair to impart semipermanent conditioning properties to the hair by contacting the hair with an aqueous or hydroalcoholic spray, solution, emulsion, and/or shampoo to treat the hair, without heat, in a rinse-off method.

BRIEF DESCRIPTION OF THE DRAWING

The above and other aspects and advantages of the present invention will become apparent from the following detailed description of the preferred embodiments illustrated in the accompanying figures, which illustrate the enhanced and durable hair conditioning properties achieved by using the method and composition of the present invention, wherein:

FIGS. 10–15 are plots showing the rating of natural, unreduced hair tresses evaluated on a scale of 1 to 6 by trained judges after treatment with a hair-treating composition, followed by one through six shampooings, respectively.

DETAILED DESCRIPTION OF THE PREFERRED EMBODIMENT

Figure 1:
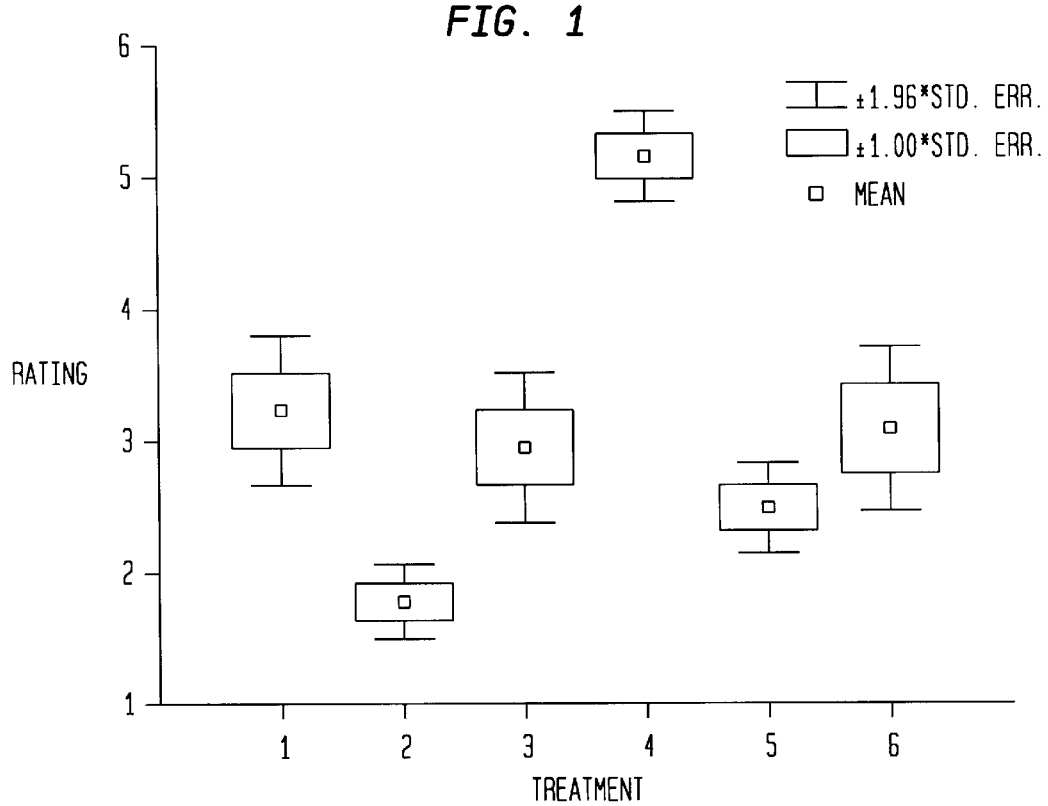
FIG. 1 is a plot showing the rating of hair tresses evaluated on a scale of 1 to 6 by trained judges after treatment with a hair-treating composition.

The hair-treating composition of the present invention is an aqueous or hydroalcoholic composition comprising a thiol-functional silicone, and has a pH of about 3 to about 9.

In particular, the present hair-treating composition comprises about 0.1% to about 5%, and preferably about 0.2% to about 4%, by weight of the composition, of a thiol-functional silicone. To achieve the full advantage of the present invention, the hair-treating composition comprises about 0.4% to about 3%, by weight, of a thiol-functional silicone. The thiol-functional silicone is capable of covalently bonding to keratin fibers, including human hair and wool.

The thiol-functional silicone is a polymeric compound, such as a thiol-functional polydimethyl-siloxane, having a weight average molecular weight ($M_w$) of about 10,000 to about 500,000, and preferably about 20,000 to about 250,000. To achieve the full advantage of the present invention, the thiol-functional silicone has an $M_w$ of about 25,000 to about 100,000.

The thiol-functional silicone contains about 0.1 mole % to about 3 mole %, and preferably about 0.2 mole % to about 2 mole %, thiol groups, i.e., —SH. To achieve the full advantage of the present invention, the thiol-functional silicone contains about 0.3 mole % to about 1 mole % thiol groups. The thiol-functional silicone also can contain amino groups, i.e., —$NH_2$, in addition to the thiol groups. The amino groups can be present in an amount of 0 mole % to about 1 mole %, and preferably 0 mole % to about 0.5 mole %, of the thiol-functional silicone.

The thiol groups provide a reactive moiety for covalently bonding the thiol-functional silicone to hair, and are present in a sufficient amount to effectively covalently bond the thiol-functional silicone to hair. The polymeric siloxane portion of the thiol-functional silicone imparts conditioning properties, such as improved combing and feel, to hair. The amino groups, if present, provide further sites for bonding the thiol-functional silicone to the hair electrostatically, and impart conditioning properties to hair that typically are associated with quaternary ammonium compounds.

An important feature of the thiol-functional silicones utilized in the present invention is the ability of the silicone to covalently bond to human hair, even if the hair is in its unreduced state. Accordingly, hair treated with a thiol-functional silicone demonstrates improved gloss, combing properties, body, and humidity resistance, without the need to subject the hair to a damaging reduction step or a damaging oxidation step. As discussed hereafter, these conditioning properties are observed on the hair after as many as five to seven hair shampooings.

A thiol-functional silicone used in the present hair-treating compositions and methods has general structural formula (I):

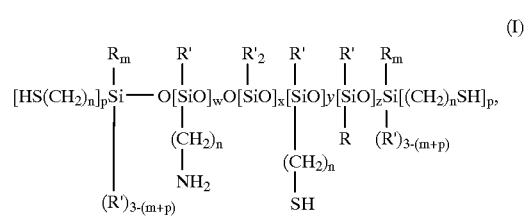

wherein R is an alkyl radical having at least 8 carbon atoms, R' is a lower alkyl radical having 1 to 7 carbon atoms, n is an integer of at least 2, m and p, independently, are 0, 1, or 2, with the proviso that the sum of m and p is not more than 2, x is an integer of at least 1, w, y, and z, independently, are 0 or an integer, and when y is 0, p is at least 1, and when z is 0, m is at least 1, wherein x is larger than the sum of w, y, and z.

In particular, the R group can be any alkyl radical having at least 8 carbon atoms, such as octyl, nonyl, decyl, hendecyl, dodecyl, tridecyl, eicosyl, heneicosyl, octadecyl, nonacosyl, triacontyl, and nonahexacontyl. A preferred R group contains 8 to about 20 carbon atoms. The R' group contains 1 to 7 carbon atoms, such as methyl, ethyl, propyl, isopropyl, butyl, isobutyl, amyl, and hexyl. Methyl is a preferred R' group.

The term n has a value of at least 2. Thus, the carbon chain to which a thiol (—SH) group or an optional amino (—$NH_2$)

group is attached has two or more carbon atoms. The carbon chain can contain up to 20 carbon atoms, however, preferred values for n are 2 and 3.

In addition, p and m, independently, are 0, 1, or 2, and the sum of m and p is not greater than 2. Therefore, the thiol-functional silicone can be endblocked with a silicon atom containing either both an R radical and a mercaptoalkyl group, or two R radicals, or two mercaptoalkyl groups. However, the sum of m and p cannot exceed 2. In addition to being endblocked by a mercaptoalkyl group and/or an R radical, these substituents can also be present along the polymeric chain. The polymeric chain also can contain alkylamino groups.

It also is envisioned that a modified thiol-functional silicone can be used in the present hair-treating compositions. In particular, it is envisioned that a portion, but not all of the thiol groups, or amino groups if present, can be interacted with a compound whereby the modified thiol-functional silicone can impart other properties to treated hair, such as style retention or color. For example, a thiol-functional silicone can be interacted with a compound capable of providing permanent or semipermanent styling or color, and having a moiety capable of reacting with a thiol or amino group. The resulting modified thiol-functional silicone then can be applied to the hair to impart durable conditioning properties and hair set retention properties.

The thiol-functional silicone typically is incorporated into a present hair-treating composition in the form of an emulsion. An aqueous emulsion of the thiol-functional silicone generally contains about 20% to about 40% by weight of the thiol-functional silicone. The aqueous emulsion is admixed with the other composition ingredients to provide a final hair-treating composition containing about 0.1% to about 5% by weight of the thiol-functional silicone.

The thiol-functional silicone emulsions are milky white compositions that are dilutable with water. The emulsifiers used in the thiol-functional silicone emulsions are nonionic and/or cationic emulsifiers, such as a mixture of trideceth-12 and cetrimonium chloride. Emulsified droplets of the thiol-functional silicone are sufficiently small to provide a stable hair-treating composition that resists phase separation, and are sufficiently large such that the predominant amount of the thiol-functional silicone does not enter the hair cuticle, but rather forms a coating on the exterior of the cuticle and is available to covalently bond to the exterior surface of the hair.

A useful emulsion containing a thiol-functional silicone is available from Dow Corning Corporation, Midland, Mich. as DC 2-8936 CATIONIC EMULSION. As discussed hereafter, the thiol-functional silicone present in DC 2-8936 imparts durable conditioning properties to hair in an unreduced state and to hair that has been reduced by a reducing lotion. In accordance with an important feature of the present invention, it has been found that thiol-functional silicones can bond to hair to impart conditioning properties that are retained through many shampooings without the need to subject the hair to a harmful chemical reduction and oxidation processes.

The pH of the present hair-treating compositions is about 3 to about 9, and preferably about 4 to about 9. To achieve the full advantage of the present invention, the pH of the composition is about 5 to about 8. Above a pH of about 9, the thiol-functional silicones have a tendency to degrade, and, accordingly, performance of the hair-treating composition is adversely affected. At a pH below about 3, the hair can be protonated or damaged.

The utility of the methods and compositions of the present invention over such a broad pH range permits the incorporation of a wide variety of beneficial optional components and additives into the hair-treating composition, without adversely affecting the basic ability of the hair-treating composition to impart durable hair conditioning properties to treated hair.

Therefore, other common cosmetic components and additives that can be incorporated into a hair-treating composition of the present invention, as long as the basic properties of the hair-treating composition are not adversely affected, include, but are not limited to, commonly used fragrances, dyes, hair colorants, opacifiers, pearlescing agents, dandruff control agents, hydrotropes, foam stabilizers, solubilizers, preservatives, water softening agents, acids, bases, buffers, and the like. These optional components and additives traditionally are present in the compositions in weight percentages of 0% to about 2% each, and about 5% to about 10% in total.

The hair-treating composition vehicle is predominantly water, but organic solvents also can be included in the aqueous hair-treating compositions in order to solubilize compounds that are not sufficiently soluble in water. Suitable organic solvents include the lower alcohols like ethyl alcohol and isopropyl alcohol, polyols like glycerol or glycols, like ethylene glycol and propylene glycol, glycol ethers, like 2-butoxyethanol, ethylene glycol, monoethyl ether, and diethylene glycol monoethyl ether or monomethyl ether, and mixtures thereof. Preferred organic solvents are the lower alcohols. These organic solvents can be present in a hair-treating composition of the present invention in an amount 0% to about 25% by weight of the composition.

The hair-treating compositions of the present invention also can be thickened, for example, with sodium alginate, guar gum, xanthan gum, gum arabic, a cellulose derivative such as methylcellulose, hydroxyethylcellulose, hydroxypropylmethylcellulose, and carboxymethylcellulose, polyoxyethylene, hydroxypropyl guar gum, starch and starch derivatives, locust bean gum, electrolytes like sodium or ammonium chloride, saccharides like glucose, and polymeric thickeners, such as polyacrylic acid derivatives. These thickeners are present in an amount of 0% to about 3%, by weight of the composition.

The hair-treating compositions also can include anionic, amphoteric, or nonionic surfactants to impart cleansing and/or emulsifying properties to the composition. Likewise, the compositions can contain other emulsifiers, silicones, fatty alcohols, humectants, and similar compounds to provide conditioning properties, esthetic properties, and desirable physical properties to the composition. Generally, such optional ingredients are present in weight percentages of 0% to about 10% each, and 0% to about 20% in total, by the total weight of the composition.

For example, representative nonionic surfactants that can be included in the hair setting composition of the present invention include esters of polyols and sugars, the polyethoxylated and/or polypropoxylated alkylphenols, the polyhydroxylated polyethers of fatty alcohols, fatty acid alkanolomides, amine oxides, and the condensation products of ethylene oxide with long chain amides. Similarly, representative anionic surfactants include alkali metal salts, ammonium salts, or salts of amines or amino alcohols of fatty acids, such as oleic acid, of the sulfates of fatty alcohols, principally $C_{12}$–$C_{14}$ and $C_{16}$ fatty alcohols, of the sulfates of polyethoxylated fatty alcohols, of the alkylbenzenesulfonates, such as those wherein the alkyl moiety has 12 carbon atoms, or of the alkylarylpolyether sulfates and monoglyceride sulfates. Other anionic surfactants include, but are not limited to, alkyl succinates, alkyl sulfosuccinates, and N-alkyl sarcosinates. Amphoteric surfactants include, but are not limited to, betaines, sultaines, cycloimidates, alkamphocarboxyglycinates, and alkamphocarboxypropionates.

Cationic conditioning compounds, like quaternary ammonium compounds, also can be incorporated into the hair-treating compositions to impart a particular hair conditioning property. All these nonionic, amphoteric, anionic, and cationic compounds, as well as numerous others not cited here, are well known in the art and are fully described in the literature.

Furthermore, water-insoluble conditioning agents, such as silicones and hydrocarbons, can be incorporated into the present hair-treating compositions. Water-insoluble conditioning agents that can be incorporated into a present hair-treating composition include, but are not limited to, a volatile or nonvolatile silicone compound, a volatile or nonvolatile hydrocarbon compound, or mixtures thereof. The volatile silicone compounds can be a linear or cyclic polydimethylsiloxane, such as hexamethylsiloxane or a cyclomethicone, available commercially under the tradenames such as DOW CORNING 200 FLUID, DOW CORNING 245 FLUID, DOW CORNING 344 FLUID, and DOW CORNING 345 FLUID from Dow Corning Corporation, Midland, Mich., and SILICONE SF-1173 and SILICONE SF-1202 from General Electric, Waterford, N.Y.

Volatile hydrocarbon compounds include hydrocarbons having about 10 to about 30 carbon atoms, for example, isododecane and isohexadecane, i.e., PERMETHYL 99A, PERMETHYL 101A, and PERMETHYL 102A, available from Presperse, Inc., South Plainfield, N.J., or an aliphatic hydrocarbon having about 12 to about 24 carbon atoms, and having a boiling point of about 100° C. to about 250° C. One such compound is ISOPAR M (a $C_{13}$–$C_{14}$ isoparaffin available from Exxon Chemical Co., Baytown, Tex.). Other exemplary volatile hydrocarbon compounds are depicted in general structural formula (II), wherein n ranges from 2 to 5.

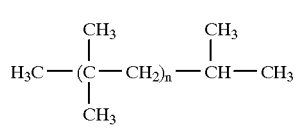

(II)

Nonvolatile hydrocarbon compounds include mineral oil, a phenyltrimethicone, or a polydimethylsiloxane having a viscosity at 25° C. of about 6 to about 400 cs, such as DOW CORNING 556 FLUID or DOW CORNING 200 FLUID, respectively, available from Dow Corning Corp., Midland, Mich.

Examples of other water-insoluble conditioning agents that can be incorporated into the present hair-treating compositions include, but are not limited to, branched 1-decene oligomers, like 1-decene dimer or a polydecene; and water-insoluble emollients, such as an ester having at least about 10 carbon atoms, and preferably about 10 to about 32 carbon atoms. Suitable esters include those comprising an aliphatic alcohol having about eight to about twenty carbon atoms, and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight-chained or branched. Preferably, the ester has a molecular weight of less than about 500 and provides emollient properties. Suitable esters, therefore, include, for example, but are not limited to: (a) aliphatic monohydric alcohol esters, including, but not limited to, myristyl propionate, isopropyl isostearate, isopropyl myristate, isopropyl palmitate, cetyl acetate, cetyl propionate, cetyl stearate, isodecyl neopentonoate, cetyl octanoate, isocetyl stearate; (b) aliphatic di- and triesters of polycarboxylic acids, including, but not limited to, diisopropyl adipate, diisostearyl fumarate, dioctyl adipate, and triisostearyl citrate; (c) aliphatic polyhydric alcohol esters, including, but not limited to, propylene glycol dipelargonate; (d) aliphatic esters of aromatic acids, including, but not limited to, $C_{12}$–$C_{15}$ alcohol esters of benzoic acid, octyl salicylate, sucrose benzoate, and dioctyl phthalate. Numerous other esters are listed in the CTFA *Cosmetic Ingredient Handbook, First Ed.*, The Cosmetic Toiletry and Fragrance Assn., Inc., Washington, D.C. (1988) at pages 24 through 26, incorporated herein by reference.

The present hair-treating compositions are prepared by simply admixing composition ingredients to provide a homogeneous composition. The resulting hair-treating composition then can be used to treat the hair by one of three different methods.

In one method, the hair first is reduced with a waving lotion. After rinsing the waving lotion from the hair, the reduced hair is contacted with a present hair-treating composition comprising a thiol-functional silicone, as a middle hair-treating step, i.e., a mid step, between hair reduction with a waving lotion and hair oxidation with a neutralizing solution or a water rinse. Then, the treated hair is contacted with a neutralizing solution. When the hair is reduced with a waving lotion containing a bisulfite salt, a water wash is sufficient, and contact with a neutralizing solution after the mid step is unnecessary. It has been found that this method covalently bonds a thiol-functional silicone to the hair, and outperforms a method wherein the reducing agent and thiol-functional silicone are applied to the hair simultaneously.

In a second method, the hair-treating composition is applied to unreduced hair by simply applying the composition onto the hair, allowing the composition to contact the hair for a sufficient time for the thiol-functional silicone to covalently bond to the hair (e.g., about 5 to about 30 minutes), then rinsing the composition from the hair with a water wash. This method is identical to the presently practiced conventional method of applying a rinse-off conditioner to the hair. However, it has been found that a present hair-setting composition containing a thiol-functional silicone unexpectedly imparts durable conditioning properties to keratin fibers, including hair and wool.

In a third method, the hair-treating composition is applied to unreduced hair as in the above-described second method, then the treated hair is contacted with a neutralizing solution. It is theorized that optionally contacting the hair with the neutralizing solution increases the amount of thiol-functional silicone covalently bonded to the hair.

Surprisingly, regardless of the method used to apply the hair-treating composition to the hair, treated hair exhibits durable conditioning properties through at least six shampooings. The tests and compositions illustrating these unexpected results are set forth below.

In one set of experiments, commercial hair tresses first were reduced with a waving lotion, then contacted with a hair-treating composition of the present invention. In this experiment, commercial hair tresses (2 grams each) were divided into six equal lengths, which were shampooed with one cubic centimeter (cc) of FINESSE EXTRA BODY SHAMPOO, available from Helene Curtis, Inc., Chicago, Ill. During the shampoo, each tress was stroked ten times, then rinsed with water for about 15 seconds.

The individual lengths of the hair tresses were treated by one of six methods. The tests were performed in triplicate, and the treated hair tresses were evaluated by three different panels of trained judges.

| Treatment No. | Waving Lotion | Mid-Step Treatment | Neutralizing Solution |
|---|---|---|---|
| 1 | Commercial Waving Lotion[1] containing 2 wt % DC 2-8936 Emulsion[2] | None | Hydrogen peroxide neutralizer with quaternary ammonium compound[3] |
| 2 | Commercial Waving Lotion[1] | 2 wt % DC 2-8936 Emulsion[4] | Hydrogen peroxide neutralizer with quaternary ammonium compound[5] |
| 3 | Commercial Waving Lotion[1] | None | Hydrogen peroxide neutralizer with thiol-functional silicone[6] |
| 4 | Commercial Waving Lotion[1] | None | Hydrogen peroxide[7] |
| 5 | Commercial Waving Lotion[1] | None | Hydrogen peroxide neutralizer with quaternary ammonium compound[5] |
| 6 | Commercial Waving Lotion[1] | 2 wt % DC 2-8936 Emulsion[8] | Hydrogen peroxide neutralizer with quaternary ammonium compound[5] |

[1]QUANTUM FIRM OPTIONS ALKALINE BUFFERED WAVE, available from Helene Curtis, Inc., Chicago, IL, containing ammonium thioglycolate and diammonium dithioglycolate;
[2]DC 2-8936 contains 35% by weight of a thiol-functional silicone, accordingly 0.70% by weight of active thiol-functional silicone is present in the wave lotion of treatment 1;
[3]Aqueous composition containing 2.1% by weight hydrogen peroxide, pH-3.4, and 0.75% dicetyldimonium chloride;
[4]0.70% by weight active thiol-functional silicone, pH-4.7;
[5]Aqueous composition containing 2.1% by weight hydrogen peroxide, pH-3.4, 0.70% by weight amodimethicone (amino-functional silicone), and 0.75% dicetyldimonium chloride;
[6]Aqueous composition containing 2.1% by weight hydrogen peroxide, pH-3.4, and 0.70% by weight thiol-functional silicone, and 0.75% dicetyldimonium chloride;
[7]2.2% by weight aqueous hydrogen peroxide; and
[8]0.70% by weight active thiol-functional silicone, pH-8.1.

After treatment, the tresses were allowed to air dry overnight. The tresses then were evaluated subjectively by panels of seven trained judges. During the evaluation, the tresses were initially rewet, and then rewet as necessary for wet combing evaluation.

After an initial evaluation, the 18 hair tresses (i.e., 6 treatments, 3 replicate samples) were simultaneously soaked at about 80° F. in an aqueous solution containing about 10% by weight of a commercial shampoo for about 10 minutes, followed by immersion into warm deionized water. Next, the tresses were rinsed a second time by immersion into a second water bath to ensure a thorough and proper rinsing. The hair tresses then were evaluated a second time by the panelists.

After this evaluation, the hair tresses were allowed to dry overnight. Then the hair tresses were subjected to a second shampooing, which was identical to the first shampooing. The hair tresses then were evaluated a third time by the panelists.

The panelists rated the hair tresses on a scale of 1 (best) to 6 (worst). Treatment 5, in which reduced hair was oxidized by a prior art neutralizing solution containing hydrogen peroxide, a quaternary ammonium compound, and amodimethicone, was used as a positive control sample. Treatment 4, in which reduced hair was oxidized by hydrogen peroxide alone, was used as a negative control sample.

A statistical analysis of the ratings revealed that the panelists ranked hair tresses treated by Treatment 4 in the worst condition (i.e., sixth), whereas hair tresses treated by Treatment 5 had the second best condition. The panelists further ranked hair tresses treated by Treatment 2, in which reduced hair was treated with a thiol-functional silicone at pH 4.6 prior to neutralization with hydrogen peroxide, a quaternary ammonium compound, and amodimethicone, as the best conditioned hair. These results are illustrated in the box and whisker plot of FIGS. 1–3. FIG. 1 shows that hair tresses treated by Treatment 2, and prior to a shampooing, had an initial average rating of about 1.8, whereas hair tresses treated by Treatment 4 had an average rating of about 5.1, and hair tresses treated by Treatment 5 had a rating of about 2.4.

Figure 2:
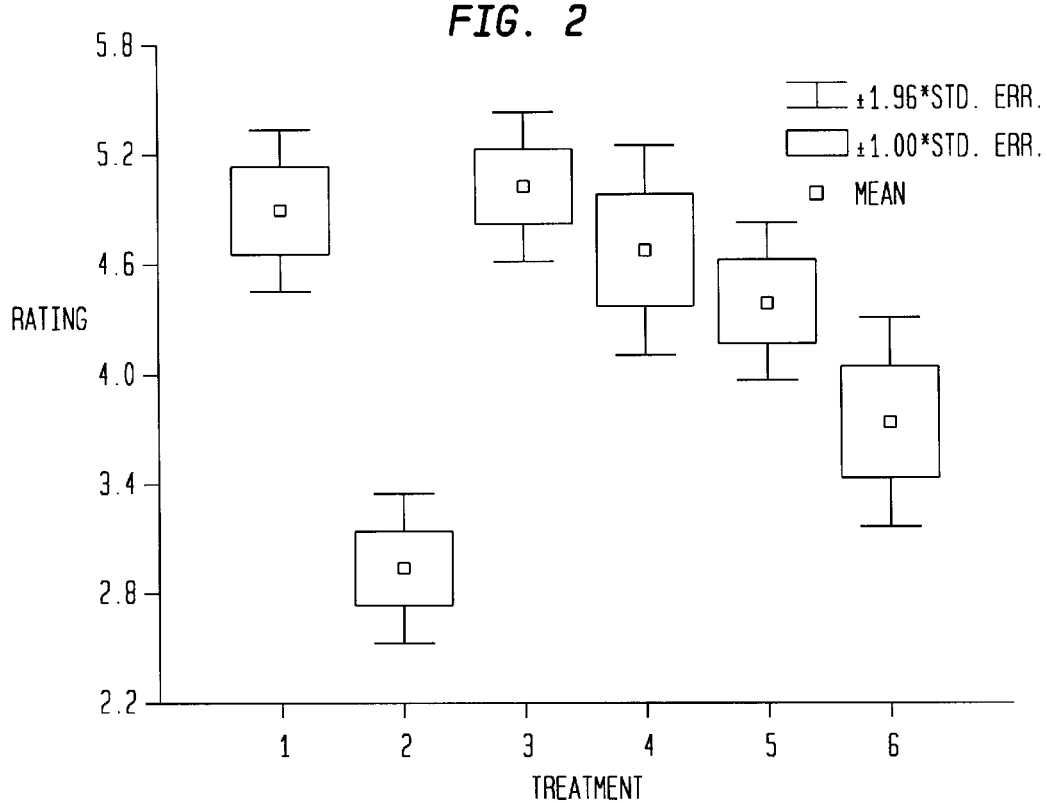
FIGS. 2 and 3 are plots showing the rating of hair tresses evaluated on a scale of 1 to 6 by trained judges after treatment with a hair-treating composition, followed by one or two shampooings, respectively.
Figure 3:
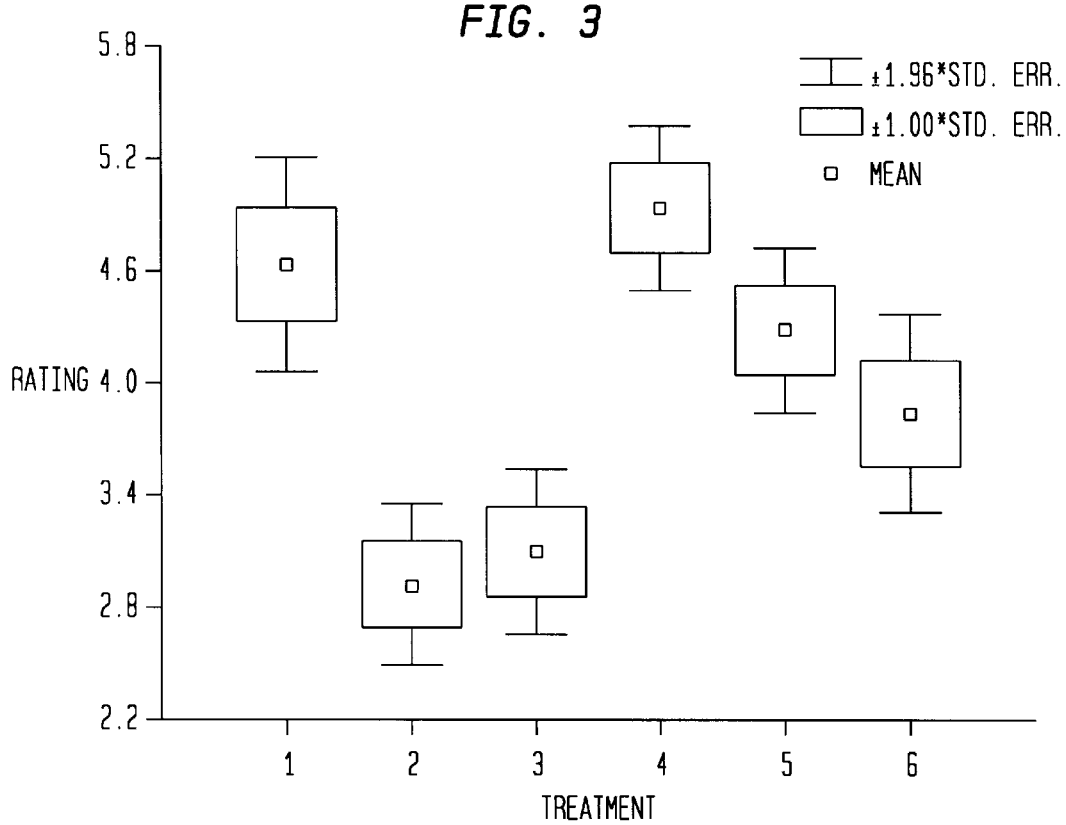
Figure 4:
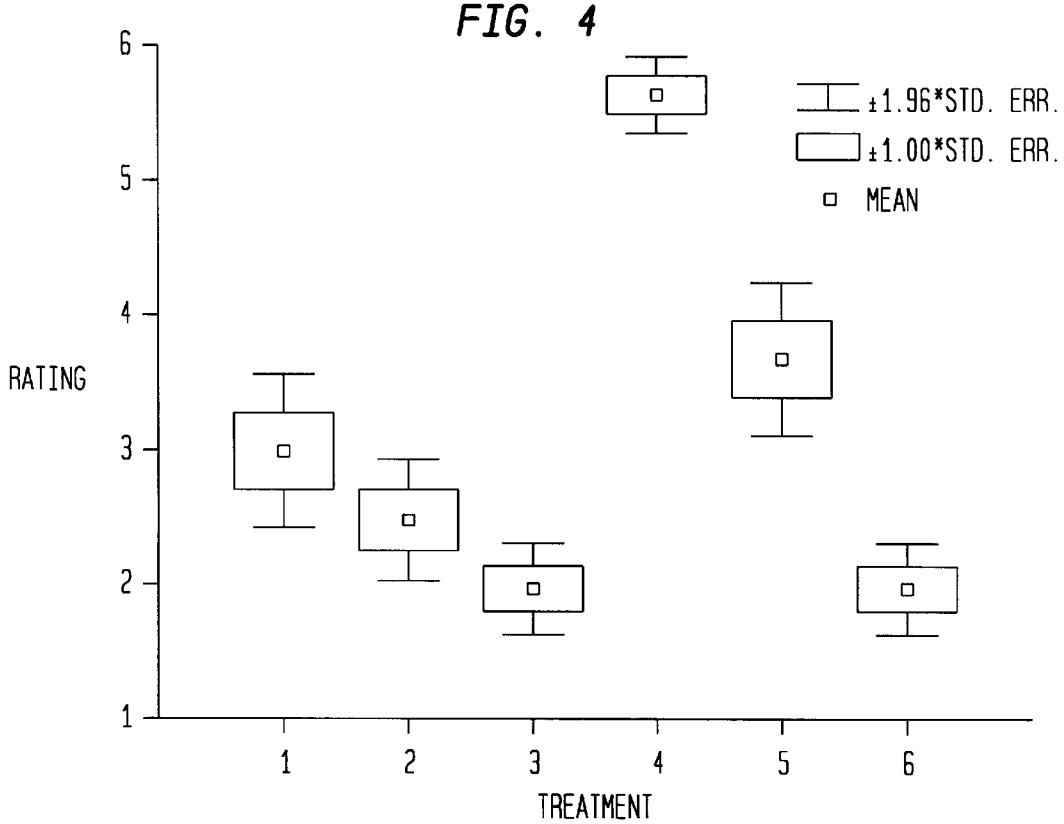
FIG. 4 is a plot showing the rating of hair tresses evaluated on a scale of 1 to 6 by trained judges after treatment with a hair-treating composition.
Figure 5:
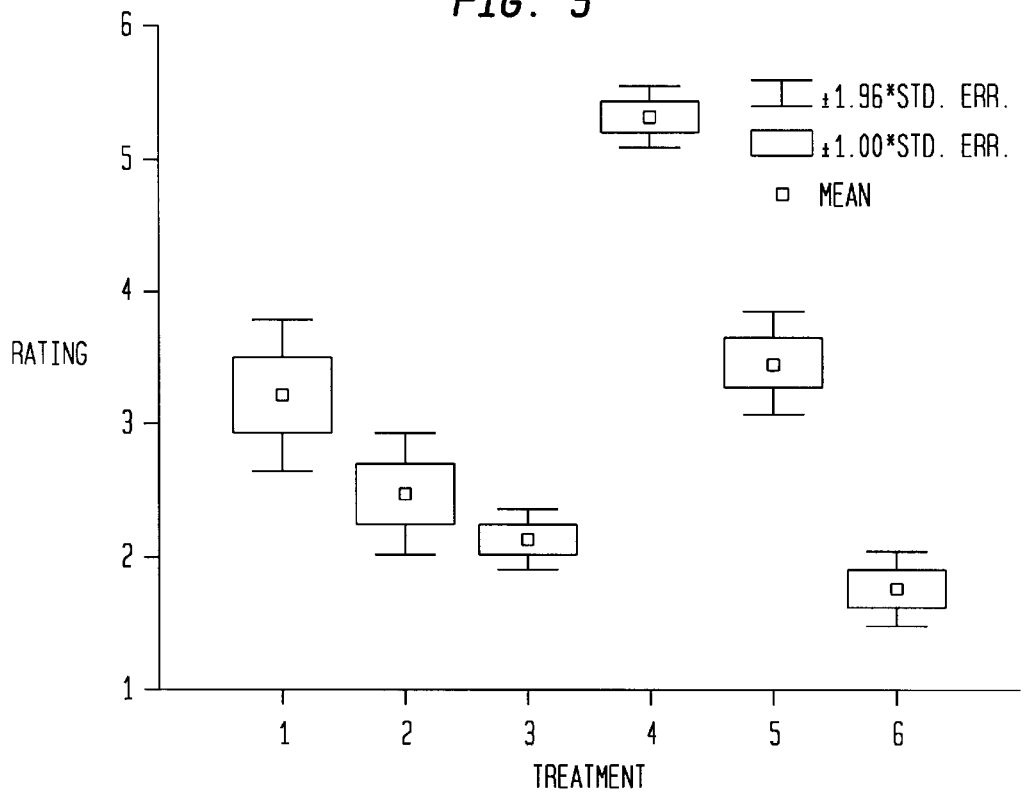
FIGS. 5–7 are plots showing the rating of hair tresses evaluated on a scale of 1 to 6 by trained judges after treatment with a hair-treating composition, followed by one, two, or three shampooings, respectively.
Figure 6:
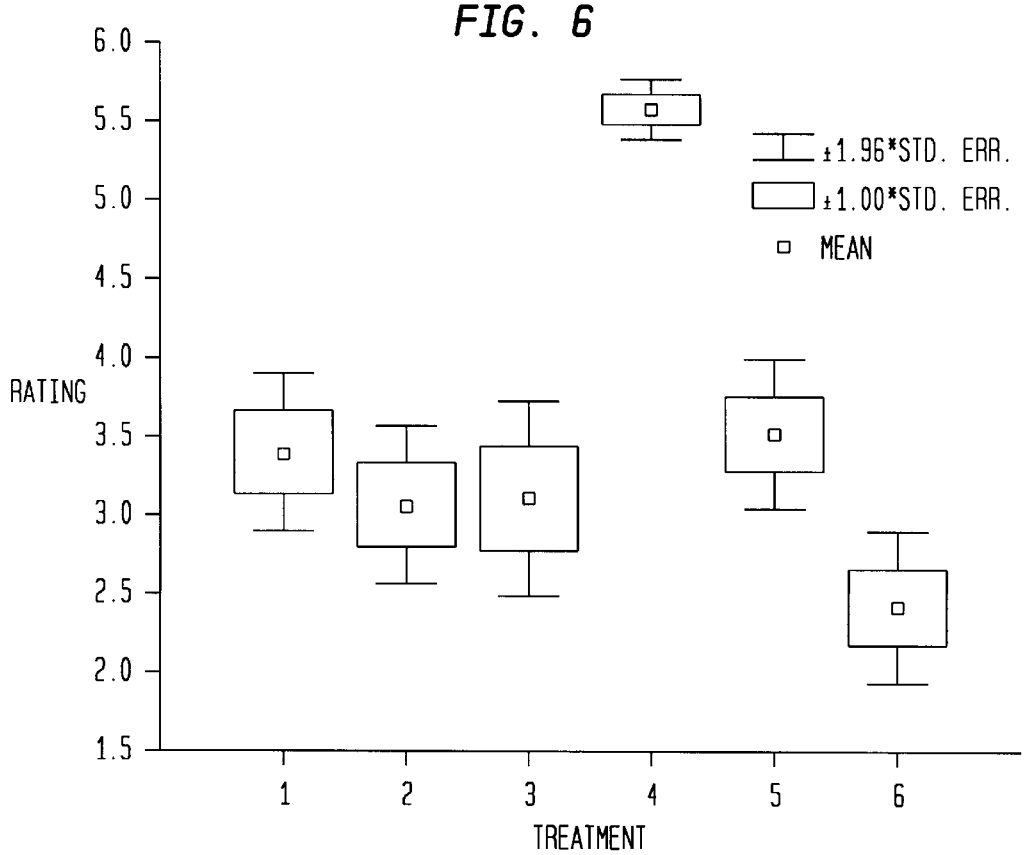
Figure 7:
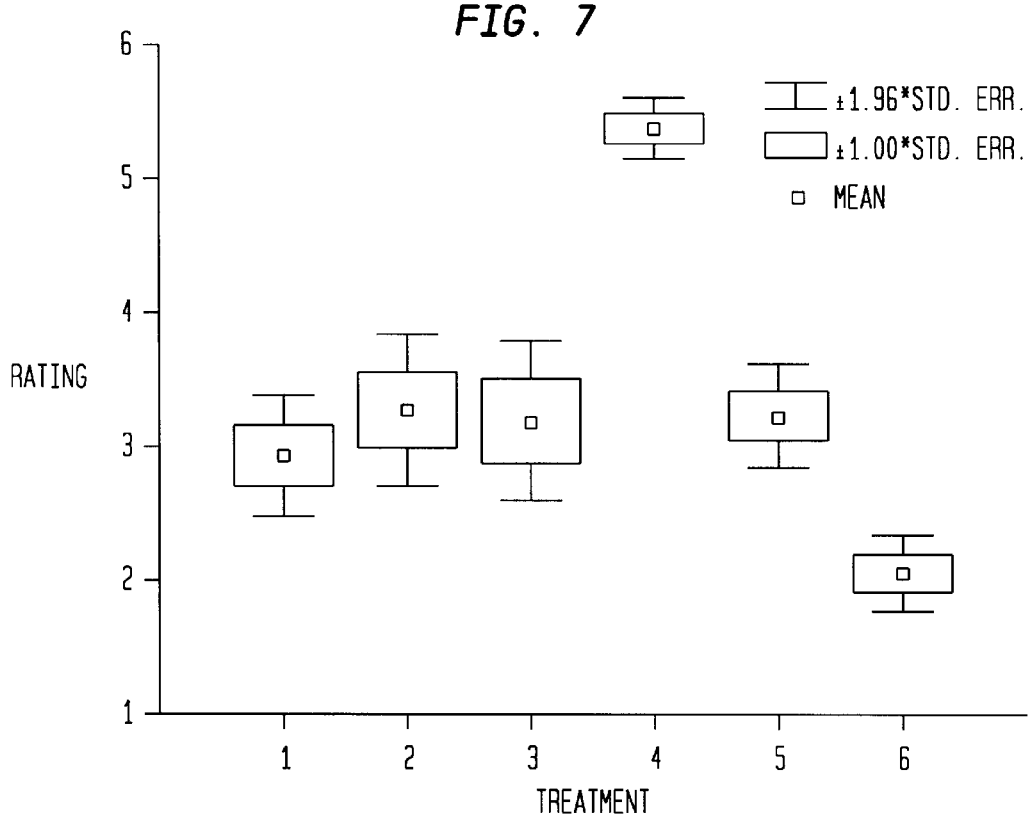

The box and whisker plot of FIG. 2 illustrates ratings after shampooing the treated tresses one time. Again, the hair tresses treated by Treatment 2 had the best conditioning properties, showing that the thiol-functional silicone remains on the hair to condition the hair through a shampooing cycle. The plot of FIG. 3 again shows that tresses treated by Treatment 2 provided the best conditioned hair. FIG. 3 illustrates the ratings after the treated tresses have been shampooed two times, thereby showing the durable conditioning properties imparted to the hair tresses by a thiol-functional silicone. FIGS. 1–3 further show that a treatment in which the thiol-functional silicone is applied to hair after hair reduction (i.e., Treatment 2) outperforms a treatment in which the reducing agent and thiol-functional silicone are applied to the hair simultaneously (i.e., Treatment 1).

In a second set of experiments, six hair tresses, in triplicate, again were treated by one of six different hair treatments. The six hair treatments were identical to Treatments 1–6 described above, except the waving lotion used in Treatment 1 did not incorporate a thiol-functional silicone and the neutralizing solution used in Treatments 2 and 6 did not contain amodimethicone.

In this set of experiments, the tresses were cut into 6-inch standard lengths and shampooed with SUAVE CLARIFYING SHAMPOO, available from Helene Curtis, Inc., Chicago, Ill. Then each tress was treated with QUANTUM FIRM OPTIONS ALKALINE WAVE (2 cc) and processed for 20 minutes. The tresses then were rinsed with warm water for 30 seconds. Tresses requiring a mid-step, i.e., Treatments 2 and 6, were treated and allowed to stand 5 minutes, followed by rinsing with warm water for 30 seconds. Next, the tresses were neutralized for 5 minutes with the appropriate neutralizing solution, followed by rinsing with warm water for 30 seconds. All treatments were conducted in triplicate.

Tresses treated by Treatments 1–6 were evaluated initially and after each of three subsequent shampooings by trained judges. The method of shampooing the tresses is described above, and the tresses were allowed to dry overnight after each shampooing and evaluation. Trained judges evaluated the tresses on a rating scale of 1 (best) to 6 (worst), with Treatment 4 being a negative control (i.e., usual rating of 5–6) and Treatment 5 being a positive control (i.e., usual rating of 1–2).

A statistical analysis of the ratings showed that hair tresses treated with a thiol-functional silicone had an excellent initial rating, and excellent ratings after each of the three shampooings. The treatment with a thiol-functional silicone outperformed treatments wherein reduced hair is treated with amodimethicone, an amino-functional silicone (i.e., Treatment 3 outperformed Treatment 5). Hair tresses treated using Treatment 3 also showed that treating reduced hair with a neutralizing solution containing a thiol-functional silicone imparted durable hair conditioning properties to treated hair. The statistical data also indicated that treating hair with a thiol-functional silicone at a pH of about 5 to about 8.1 imparts more durable hair conditioning properties to the hair.

FIGS. 4–7 are box and whisker plots summarizing the hair tress evaluations discussed above for initially treated hair tresses, and after one, two, and three shampooings, respectively. FIGS. 4–7 illustrate that hair treated with a thiol-functional silicone exhibits durable hair conditioning properties that withstand numerous shampooings.

Figure 8:
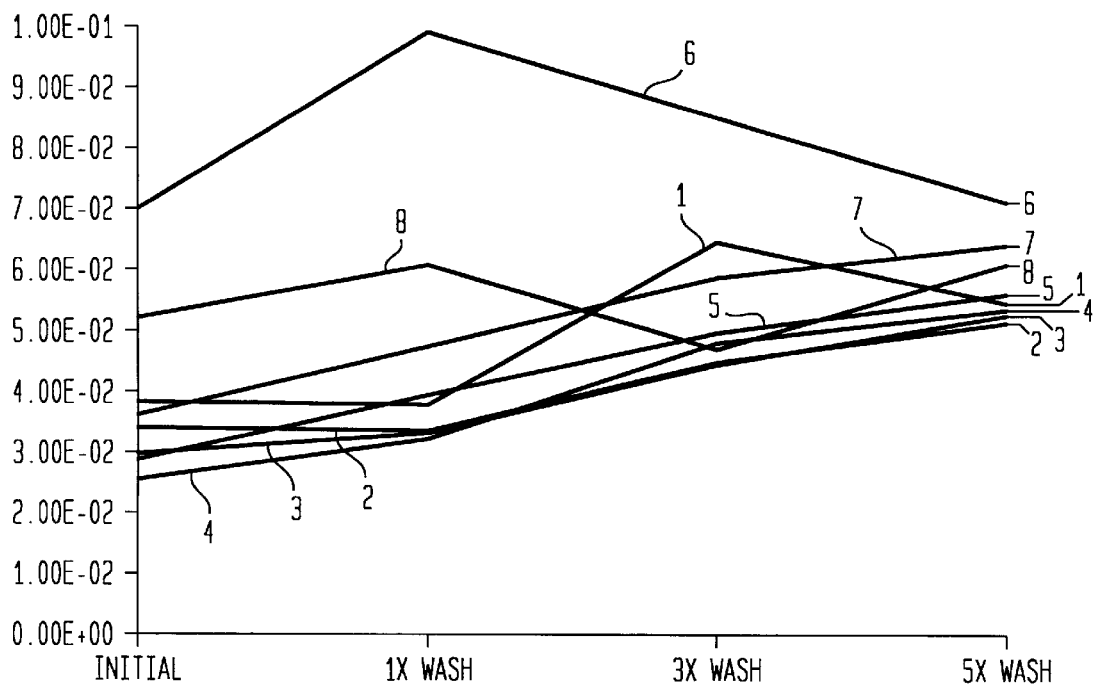
FIG. 8 is a plot of number of shampooings vs. work needed to comb tresses treated with a hair-treating composition.

In a third set of experiments, the effect of pH on treating reduced hair with a thiol-functional silicone, either prior to neutralization or contemporaneously with neutralization. In particular, the tresses initially were washed to strip the untreated commercial tresses of residual contaminants, such cationics and naphthalenes, prior to testing. The stripping procedure utilizes a wash with an anionic surfactant (i.e., sodium lauryl sulfate), followed by a wash using a nonionic surfactant (i.e., nonoxynol-10) and isopropyl alcohol. Then, three replicate sets of individual hair tresses were treated by one of the following eight treatments.

was performed on a DIA STRON Miniature Tensile Tester, which measures the total work required to comb a wet hair tress. The lower the total amount of work required, the better the wet combing properties of the hair. FIG. 8 illustrates that reduced hair tresses treated with a thiol-functional silicone, either as a mid-step or in the neutralizing solution (i.e., Treatments 1–5) exhibited better hair conditioning properties after five washings than Treatments 6–8. Accordingly, treating hair with a composition containing a thiol-functional silicone imparts durable hair conditioning properties to treated hair. Furthermore, FIG. 8 illustrates that the present hair treating compositions impart durable hair-conditioning properties and a pH of about 3 to about 9, and especially at a pH of about 5 to about 9.

The treated tresses also were tested by Diffuse Reflectance Infrared Fourier Transform Spectroscopy (DRIFTS) to determine the amount of conditioning agent present on individual hair tresses. In this test, the ratio of the area of the silicon methyl (SiMe) infrared peak at 1260 $cm^{-1}$ to the area of the Amide III infrared peak of hair keratin at 1240 $cm^{-1}$, and used as the internal standard, was calculated from the following equation for each hair tress using the second derivative spectrum. These ratios, or silicone indexes, are correlated to ppm (parts per million) silicon deposited on tresses, as determined by atomic absorption spectroscopy, with a linear correlation from 40 ppm to 170 ppm silicon.

$$\text{Silicone Index} = \frac{\text{Area of SiMe peak at 1260 } cm^{-1}}{\text{Area of Amide III peak at 1240 } cm^{-1}}$$

The tests showed that silicone remained on all hair tresses treated with a thiol-functional silicone as a mid-step (i.e., Treatments 1–4) through five washings, whereas a first washing removed silicone from the tresses treated with a neutralizing solution containing a silicone (i.e., Treatment 7). The greatest amount of silicone remained on hair tresses treated with a composition containing a thiol-functional silicone and having a pH 9.

| Treatment No. | Waving Lotion | Mid-Step | Neutralizer |
|---|---|---|---|
| 1 | Commercial Waving Lotion[1] | Thiol-functional silicone[2], pH-3 | Hydrogen peroxide neutralizer[3] |
| 2 | Commercial Waving Lotion[1] | Thiol-functional silicone[2], pH-5 | Hydrogen peroxide neutralizer[3] |
| 3 | Commercial Waving Lotion[1] | Thiol-functional silicone[2], pH-7 | Hydrogen peroxide neutralizer[3] |
| 4 | Commercial Waving Lotion[1] | Thiol-functional silicone[2], pH-9 | Hydrogen peroxide neutralizer[3] |
| 5 | Commercial Waving Lotion[1] | None | Hydrogen peroxide neutralizer[5] |
| 6 | Commercial Waving Lotion[1] | None | Hydrogen peroxide neutralizer[7] |
| 7 | Commercial Waving Lotion[1] | None | Hydrogen peroxide neutralizer[6] |
| 8 | Untreated tresses | — | — |

In these experiments, each hair tress was treated with QUANTUM FIRM OPTIONS waving lotion (2 cc/2 grams of hair) and processed for 20 minutes. The tresses then were rinsed with water for 30 seconds. Tresses treated with a mid-step (i.e., Treatments 1–4) were blotted, treated with 2 cc of the thiol-functional silicone composition, and processed for 5 minutes. The tresses then were rinsed with water for 30 seconds. After blotting, the tresses were treated with a neutralizing solution (2 cc) and processed for 5 minutes. The hair tresses finally were rinsed for 30 seconds. The tresses were evaluated initially and after each of five shampooings, for wet combing properties and by Infrared Fourier Transform Spectroscopy (FTIR). The tresses were allowed to air dry overnight after each shampooing and evaluation.

The plots in FIG. 8 summarize the results of wet combing tests performed on the treated tresses. The wet combing test In another set of experiments, hair-treating compositions containing about 0.70% of a thiol-functional silicone, over a pH range of 3–9, were applied to unreduced hair, then the hair was treated with a neutralizing solution containing 2.1% hydrogen peroxide and dicetyldimonium chloride. These treated hair tresses were compared to hair tresses treated with amodimethicone and to untreated tresses. All the tresses then were shampooed, and rated by trained judges for wet combing.

The tresses treated with a thiol-functional silicone and having a pH of 3 or 9 outperformed hair tresses treated with amodimethicone. Tresses treated with a thiol-functional silicone and having a pH of 7 were conditioned about equally to hair treated with amodimethicone. Accordingly, it has been shown that a thiol-functional silicone is substantive to unreduced hair, and imparts durable hair conditioning properties to the hair.

In another set of experiments, compositions were prepared, then applied to unreduced hair tresses. Each composition contained 5% by weight of a thiol-functional silicone (Treatments 1–4) or an amodimethicone (Treatments 5–6). The treated hair tresses then were shampooed several times, and the conditioning properties of the treated hair tresses were tested after each shampoo.

Treatment 1—5% by weight aqueous thiol-functional silicone, pH 9

Treatment 2—5% by weight aqueous thiol-functional silicone, pH 7

Treatment 3—5% by weight aqueous thiol-functional silicone, pH 5

Treatment 4—5% by weight aqueous thiol-functional silicone, pH 3

Treatment 5—5% by weight aqueous amodimethicone, pH 9 (comparative), and

Treatment 6—5% by weight aqueous amodimethicone, pH 3 (comparative).

The compositions containing thiol-functional silicone were prepared by admixing an appropriate amount of DC 2-8936 in water and adjusting to the desired pH with phosphoric acid or sodium hydroxide. The comparative compositions containing amodimethicone were prepared by admixing an appropriate amount of DOW CORNING® 929 CATIONIC EMULSION in water and adjusting to the desired pH with phosphoric acid or sodium hydroxide.

In particular, eighteen hair tresses first were washed by the method described above to strip the commercial hair tresses of residual contaminants. The individual tresses, in three replicate experiments, were treated with 2 ml (milliliters) of one of the above six compositions. Each treated tress was placed in a plastic cap and allowed to stand at room temperature for about 10 minutes. Then, each tress was rinsed with warm water for about 30 seconds. The tresses then were evaluated subjectively by a panel of six to seven trained judges for wet combing properties. The evaluations were performed in triplicate by different panels of judges. The wet combing results were rated over a range of one (best) to six (worst).

The hair tresses then were allowed to air dry overnight. The dried tresses were shampooed and evaluated again in the same manner for wet combing properties. The procedure of air drying and shampooing was repeated over seven days and a total of ten shampooings and evaluations.

Figure 9:
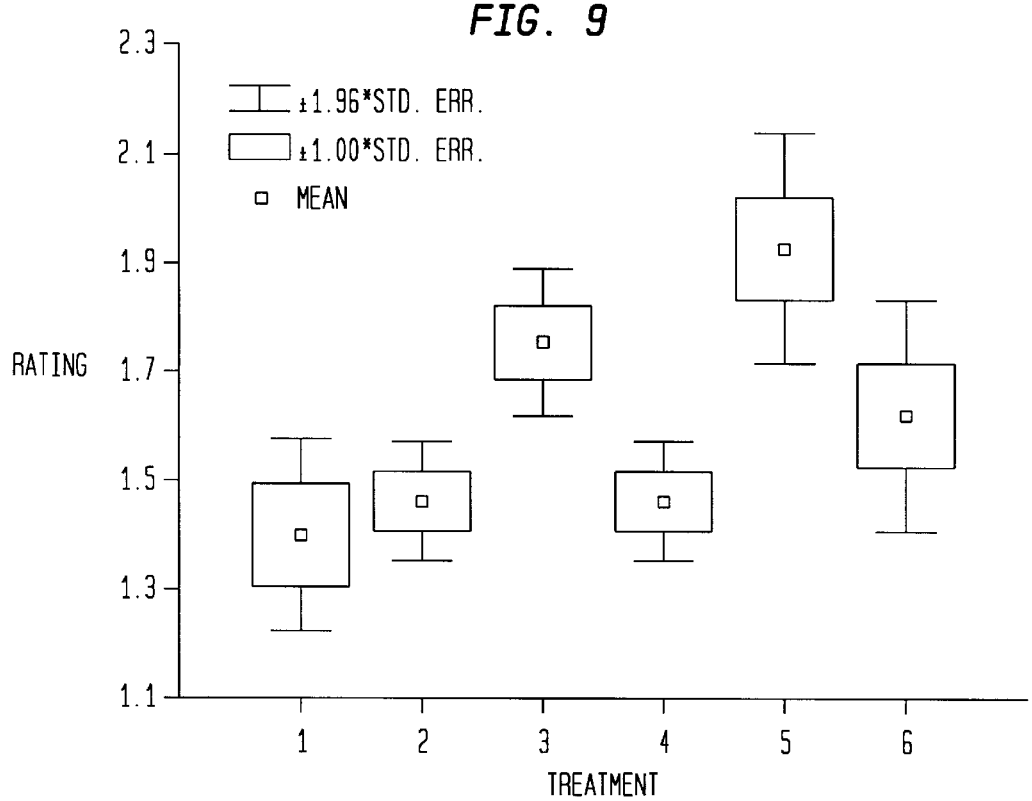
FIG. 9 is a plot showing the rating of natural, unreduced hair tresses evaluated on a scale of 1 to 6 by trained judges after treatment with a hair-treating composition.

The initial wet combing properties demonstrated by hair tresses subjected to Treatments 1 through 6, prior to any shampooings, is illustrated in FIG. 9. FIG. 9 shows that unreduced hair tresses treated with a thiol-functional silicone (i.e., Treatments 1–4) outperformed hair tresses treated with amodimethicone, an amino-functional silicone (Treatments 5 and 6). The thiol-functional silicone imparted excellent wet combing properties to treated hair tresses over the pH range of about 3 to about 9.

Figure 10:
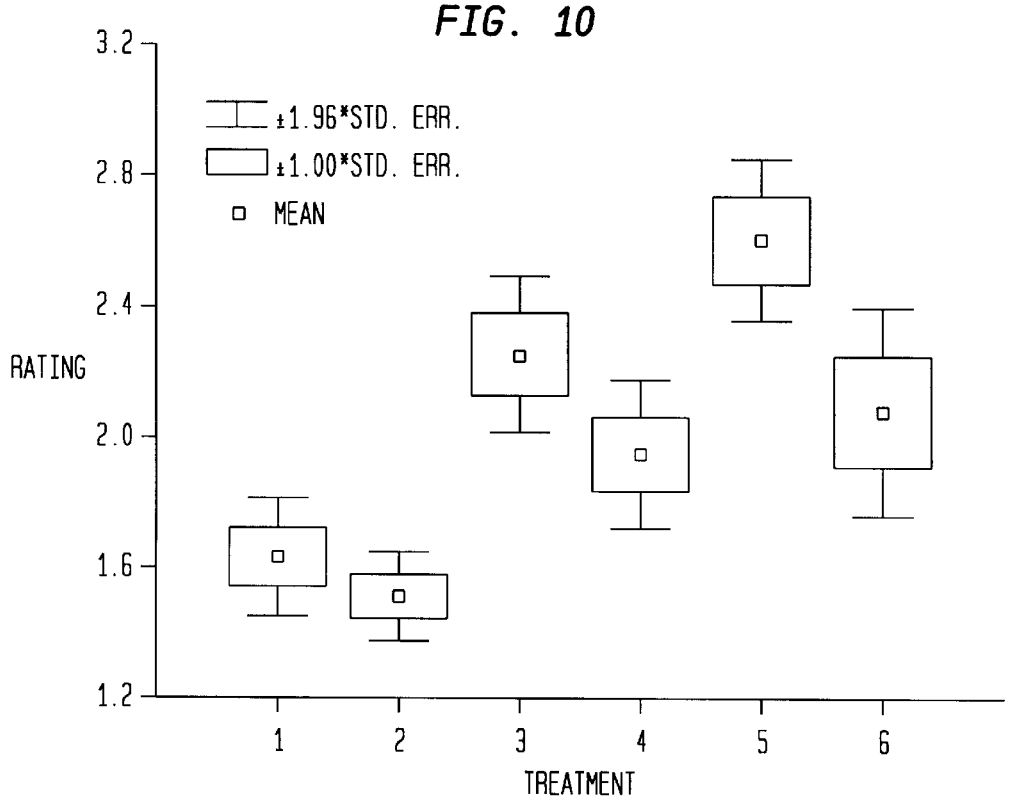
Figure 11:
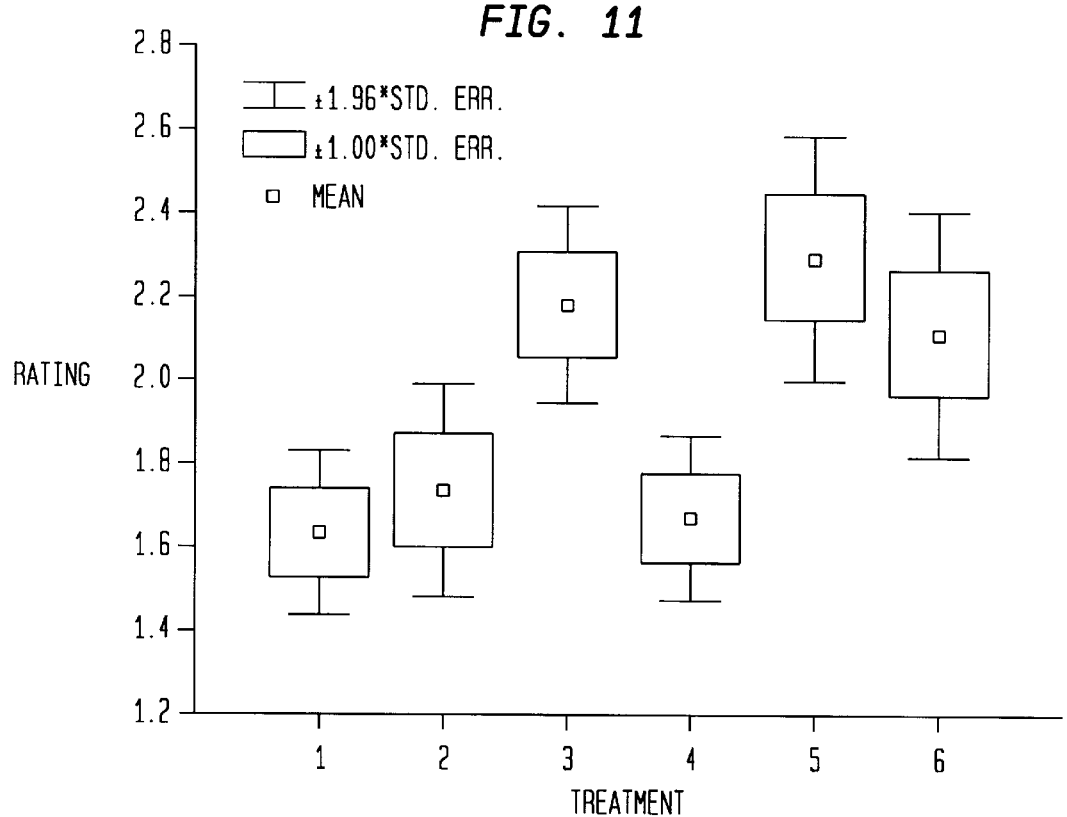
Figure 12:
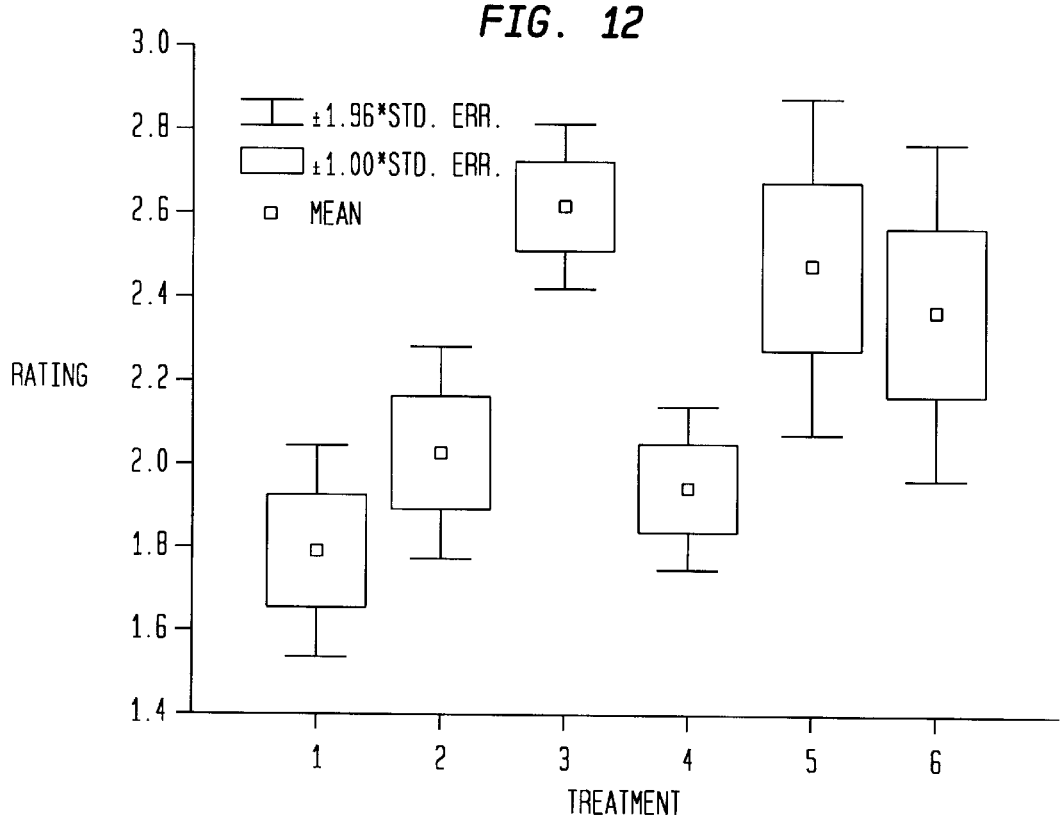
Figure 13:
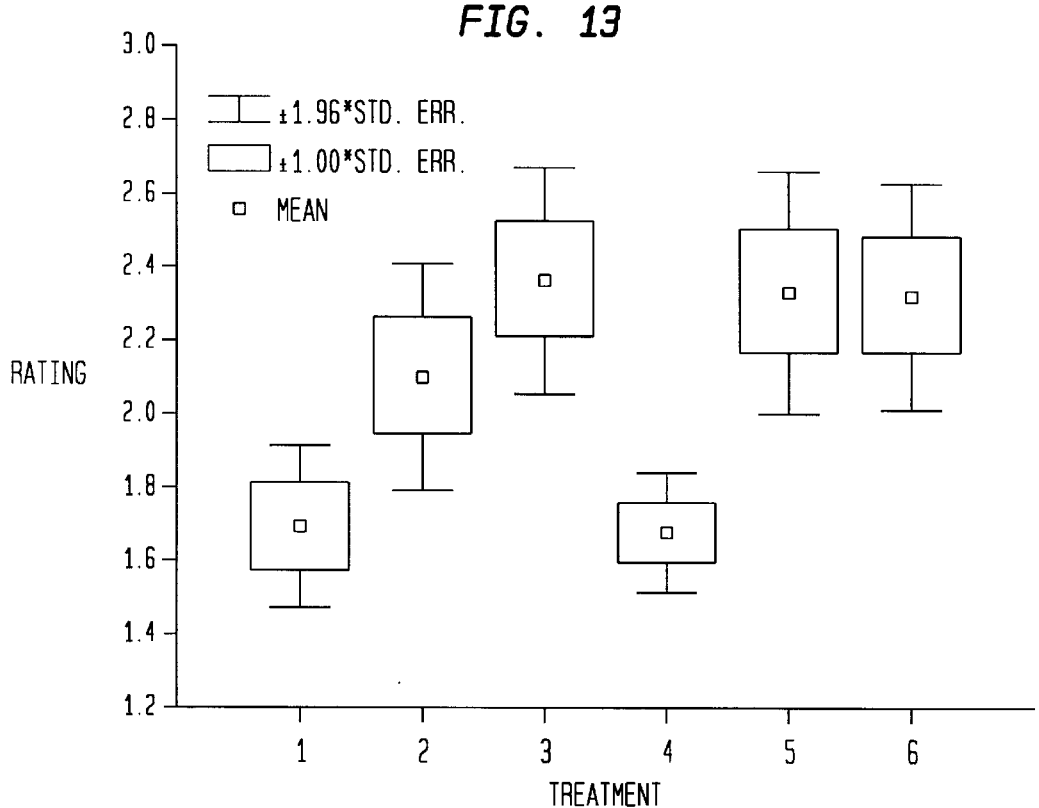
Figure 14:
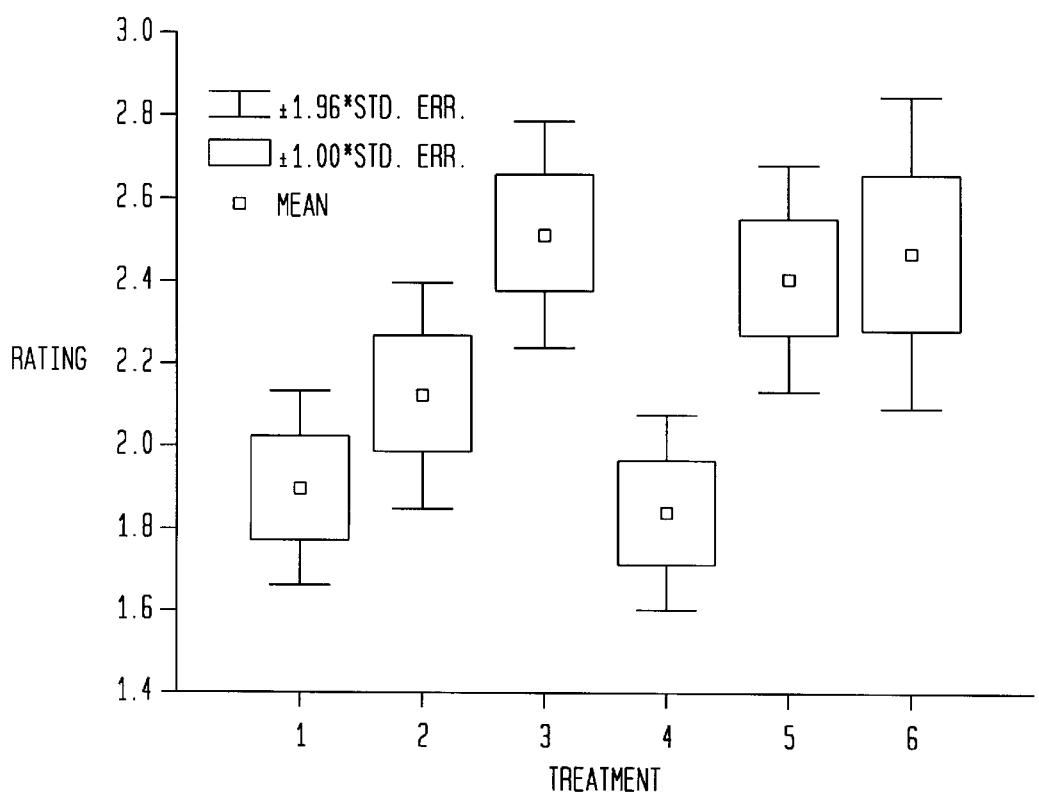

FIG. 10 shows that, after one shampooing, hair tresses treated with a thiol-functional silicone had better conditioning properties than tresses treated with amodimethicone. In particular, hair tresses treated with using a thiol-functional silicone at pH 9 and pH 7 were essentially unaffected by the shampooing, thereby showing that the thiol-functional silicone is substantive, i.e., covalently bonded, to the hair. In contrast, after one shampooing, the amodimethicone-treated hair tresses showed reduced wet combing properties.

FIGS. 11–15 similarly summarize the wet combing evaluations after two through six shampooings, respectively. FIGS. 11–15 show that hair tresses treated with a thiol-functional silicone retain excellent wet combing properties through at least six shampooings, and outperform hair tresses treated with amodimethicone. The thiol-functional silicone compounds applied using a composition having a pH of 3 and 7–9 imparted especially durable conditioning properties to treated hair. This experiment shows that a thiol-functional silicone compound can covalently bond to unreduced hair to impart durable, semipermanent conditioning properties to treated hair. Such a result is important because process steps that damage the hair, like hair reducing and hair oxidizing steps can be avoided.

Therefore, in accordance with the method of the present invention, after applying a hair-treating composition comprising a thiol-functional silicone to keratin fibers, conditioning properties of the fibers, like human hair and wool, are improved sufficiently such that the composition does not have to be reapplied to the fibers after each shampooing, and such that the desired conditioning properties have the potential to last many days and through many shampooings. Most notably, the benefits of imparting durable conditioning properties are achieved in the method of the present invention without damaging the hair through harsh chemical reduction and oxidation steps. The thiol-functional silicone contains sufficient thiol groups to provide a sufficient number of available linkages to react with the disulfide bonds in the hair. Similarly, the composition of the present invention includes a sufficient amount of the thiol-functional silicone to react with the hair in order to condition the hair and impart semipermanent conditioning properties.

In accordance with another important feature of the present invention, applying the present hair-treating composition to hair provides the benefits and advantages of improved hair conditioning and semipermanent conditioning when the composition has a pH of about 3 to about 9. The hair-treating compositions of the present invention, having a pH of about 3 to about 9, impart beneficial conditioning properties demanded by the consumer, such as combability, gloss, softness, and body.

Although there are several commercial products in the marketplace to condition the hair, such as setting lotions, gels, and hair sprays, these products must be applied to the hair after each shampoo, either prior to or during the styling process. However, in accordance with the method of the present invention, contacting the hair with a composition comprising a thiol-functional silicone provides hair conditioning properties that are semipermanent and resistant to at least three, and up to five to seven, subsequent shampooings. As a result, a hair-treating composition does not need to be reapplied to the hair after each shampooing, therefore making hair conditioning more convenient for the consumer.

In addition, the method of the present invention provides the further benefits of not leaving the hair tacky or sticky, not forming a crust, and, therefore, providing combability, and not damaging the hair. In addition, after treating the hair with the composition of the present invention, the set hair feels natural and thickened, has body, is soft, shiny, manageable, and combable, and retains a desired hair style, even under high humidity conditions. These beneficial effects can be achieved by using an aqueous or hydroalcoholic spray or solution formulation, emulsion formulation, shampoo formulation, or a suitable combination of all three formulations. In general, the benefits and advantages of the present invention can be realized regardless of the end-use hair-treating composition used to treat the hair, such as conditioners, hair sprays, shampoos, hair color, bleaches, or other fixatives.

Obviously, many modifications and variations of the invention as hereinbefore set forth can be made without department from the spirit and scope thereof, and, therefore, only such limitations should be imposed as are indicated by the appended claims.

What is claimed is:

1. A method of imparting semipermanent conditioning properties to unreduced keratin fibers comprising the steps of:

(a) contacting the fibers in their unreduced state with a hair-treating composition having a pH of about 3 to about 9 and comprising about 0.1% to about 5% by weight of a thiol-functional silicone and an aqueous carrier, for a sufficient time for the thiol-functional silicone to covalently bond to the keratin fibers, said thiol-functional silicone having a weight average molecular weight of about 10,000 to about 500,000 and having about 0.1 mole % to about 3 mole % thio groups;

(b) neutralizing the fibers contacted with the hair-treating composition; and wherein the fibers are not exposed to reducing agent during the method.

2. The method of claim 1 wherein the keratin fibers are human hair or wool.

3. The method of claim 1 wherein the composition comprises about 0.2% to about 4% of the thiol-functional silicone.

4. The method of claim 1 wherein the composition comprises about 0.4% to about 3% of the thiol-functional silicone.

5. The method of claim 1 wherein the thiol-functional silicone has a weight average molecular weight of about 20,000 to about 250,000.

6. The method of claim 1 wherein the thiol-functional silicone contains about 0.2 mole % to about 2 mole % thiol groups.

7. The method of claim 1 wherein the thiol-functional silicone contains about 0 mole % to about 1 mole % amino groups.

8. The method of claim 1 wherein the thiol-functional silicone has a structure:

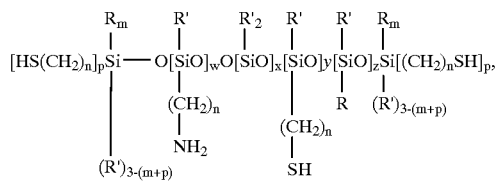

wherein R is an alkyl radical having at least 8 carbon atoms, R' is a lower alkyl radical having 1 to 7 carbon atoms, n is an integer of at least 2, m and p, independently, are 0, 1, or 2, with the proviso that the sum of m and p is not more than 2, x is an integer of at least 1, w, y, and z, independently, are 0 or an integer, and when y is 0, p is at least 1, and when z is 0, m is at least 1, wherein x is larger than the sum of w, y, and z.

9. The method of claim 1 wherein the hair-treating composition contacts the fibers for about 5 to about 30 minutes.

10. The method of claim 1 wherein the fibers contacted by the thiol-functional silicone are neutralized by rinsing the fibers with water.

11. The method of claim 1 wherein the fibers contacted by the thiol-functional silicone are neutralized by contacting the fibers with a neutralizing solution comprising hydrogen peroxide or a bromate salt.

12. The method of claim 11 wherein the neutralizing solution further comprises amodimethicone, a quaternary ammonium compound, a thiol-functional silicone, or a mixture thereof.

13. The method of claim 1 wherein the hair-treating composition further comprises a thickener, a surfactant, a water-insoluble conditioning agent, or a mixture thereof.

14. The method of claim 8 wherein the thiol-functional silicone is modified by interacting the thiol-functional silicone with a compound having a moiety capable of interacting with a thiol group or an amino group.

15. The method of claim 14 wherein the compound is capable of imparting styling or color to the keratin fibers.

* * * * *